United States Patent [19]
De Boer et al.

[11] Patent Number: 5,910,425
[45] Date of Patent: Jun. 8, 1999

[54] MICROBIAL STRAINS PRODUCING SPHINGOLIPID BASES

[75] Inventors: Lex De Boer, Wateringen; Ingrid Francisca Caroline Van Der Wildt, Delft, both of Netherlands

[73] Assignee: Gist-Brocades, N.V., Ma Delft, Netherlands

[21] Appl. No.: 08/640,941

[22] PCT Filed: Nov. 3, 1994

[86] PCT No.: PCT/EP94/03652

§ 371 Date: May 3, 1996

§ 102(e) Date: May 3, 1996

[87] PCT Pub. No.: WO95/12683

PCT Pub. Date: May 11, 1995

[30] Foreign Application Priority Data

Nov. 3, 1993 [EP] European Pat. Off. .............. 93203081
Jul. 8, 1994 [EP] European Pat. Off. .............. 94201986

[51] Int. Cl.$^6$ ....................................................... C12P 1/00
[52] U.S. Cl. ......................... 435/41; 435/128; 435/255.5; 435/938
[58] Field of Search ......................... 435/41, 128, 255.5, 435/938

[56] References Cited

U.S. PATENT DOCUMENTS 5,618,706  4/1997  Casey et al. ............................. 435/128
5,627,056  5/1997  Casey et al. ............................. 435/134

OTHER PUBLICATIONS

Barenholz et al. (1971) 248 Biochim. Biophys. ACTA 458–465, 1971.

L.J. Wickerham et al., "Formation of Extracellular Sphingolipids by Microorganisms", *Journal of Bacteriology*, 80, pp. 484–491, 1960.

Baarenholz et al. (1973) Biochim. Biophys. Acta, vol. 306, pp. 341–345, 1973.

Kaufman et al. (1971) J. Biol. Chem. vol. 246, No. 13, pp. 4266–4271, 1971.

W.J. Pinto et al., "Sphingolipid Long Chain–Base Auxotrophs of *Saccharomyces cerevisae*: Genetics, Physiology, and a Method for Their Selection", *Journal of Bacteriology*, 174(8), pp. 2565–2574, 1992.

J.D. Fishbein et al., "Ceramide–mediated Growth Inhibition and CAPP Are Conserved in *Saccharomyces cerevisiae*", *Journal of Biological Chemistry*, 268(13) pp. 9255–9261, 1993.

D.J. Bibel et al., "Antimicrobial Activity of Sphingosines", *The Journal of Investigative Dermatology*, 98(3), pp. 269–273, 1992.

Barenholz, et al., "Identificaton of the Enzymatic Lesions Responsible for the Accumulation of Acetylated Sphingosine Bases in the Yeast Hansenula Ciferri"*Biochimica Biophysica Acta* 306:341–345 (1973).

Ishida–Shick e tal., "Phytosphingosine Accumulates in Recessive Yeast Mutants that Produce Novel Endogenous Ethanolamine" *Genetics* 104:36–37 (1983).

Kaneshiro, et al., "Fumonisin–Stimulated N–Acetyldihydrosphingosine, N–Acetylphytosphingosine and Phytosphingosine Products of Pichia (Hansenula) ciferii, NRRL Y–1031" *Current Microbiology* 24:319–324 (1992).

Pinto, et al., "Characterization of Enzymatic Synthesis of Sphingolipid Long–Chain Bases in Saccharomyces Cerevisiae: Mutant Strains Exhibiting Long–Chain–Base Auxotrophy Are Deficient in Serine Palmitoyltransferase Activity" *Journal of Bacteriology* 174:2575–2581 (1992).

Thorpe, et al., "Chemistry and Metabolism of Sphingolipids. On the Biosynthesis of Phytosphingosine by Yeast" *Biochemistry* 6:887–897 (1967).

Walker, et al., "The Royal Society of Chemistry, London, GB" *Molecular Biology & Biotechnology* pp. 1–23 (1989).

Japanese Abstract JP 60–180597 A (1985).

Japanese Abstract JP 60 188085 A (1985).

*Primary Examiner*—Keith D. Hendricks
*Assistant Examiner*—Enrique D. Longton
*Attorney, Agent, or Firm*—Morrison & Foerster

[57] ABSTRACT

Microbial strains capable of producing enhanced levels of sphingosine, dihydrosphingosine, phytosphingosine and/or derivatives thereof are disclosed. Additionally, there are disclosed methods based on mutagenesis, or other selection techniques, whereby such strains can be produced. As a preferred example thereof, mutant strains of Pichia are provided that are capable of producing about 50% more of such compounds than wild type strains.

17 Claims, No Drawings

MICROBIAL STRAINS PRODUCING SPHINGOLIPID BASES

The present invention relates to methods for the improvement of microbial strains producing sphingolipid bases by means of mutagenesis and selection techniques.

BACKGROUND OF THE INVENTION

The term "sphingolipids" refers to a group of lipids which are derived from sphingosine. Sphingolipids occur frequently in the cellular membranes of animals, plants and microorganisms. The exact function of sphingolipids in humans remains unknown, but it is clear that this group of compounds is involved in the transmission of electrical signals in the nervous system and in the stabilization of cell membranes. It has also been suggested that glycosphingosines have a function in the immune system: specific glycosphingosines function as receptors for bacterial toxins and possibly also as receptors for bacteria and viruses.

Sphingolipids contain sphingosine, dihydrosphingosine or phytosphingosine as a base in amide linkage with a fatty acid. Sphingosine or phytosphingosine bases may be used as starting materials in the synthesis of a particular group of sphingolipids, namely ceramides. Ceramides are the main lipid component of the stratum corneum, the upper layer of the skin. The stratum corneum has an important barrier function, external compounds are generally kept outside of its barrier and the loss of moisture is limited. The addition of sphingolipids such as ceramides to skin cosmetic products improve the barrier function and moisture-retaining properties of the skin (Curatolo, 1987; Kerscher et al., 1991).

Currently, heterogenous sphingolipid preparations for cosmetics are mainly extracted from animal sources. Obviously, this is a rather costly process on an industrial scale. Moreover, it has been found that these materials are potentially unsafe due, for example, to the possible presence of bovine spongiform encephalomyelitis (BSE) in bovine tissue. Thus, the cosmetic industry has demonstrated an increasing interest in new sources of pure, well-defined sphingolipids, which are obtained from sources other than animal tissues.

Microorganisms such as the yeasts *Pichia ciferrii*, formerly indicated as *Hansenula ciferrii* and *Endomycopsis ciferrii* (Barnett et al., 1990; Stodola and Wickerham, 1960; Wickerham and Stodola, 1960; Wickerham et al., 1954; Wickerham, 1951) have been found to produce sphingolipids as such, as well as sphingosine, phytosphingosine and/or derivatives thereof. This discovery provides sources for sphingolipids themselves and for starting materials for the production of other commercially valuable compounds which could offer a viable alternative to the use of animal sources of these compounds.

For example, acetylated derivatives of sphingosine, dihydrosphingosine and phytosphingosine may be deacetylated and the thus-obtained sphingosine, dihydrosphingosine or phytosphingosine may be chemically converted into related compounds such as ceramides, pseudoceramides and/or glycoceramides which in turn may be applied in cosmetic and therapeutic products (Smeets and Weber, 1993).

The production of phytosphingosine and/or its acetylated derivatives has also been demonstrated in the yeasts *Candida utilis* and *Saccharomyces cerevisiae* (Wagner and Zofcsik, 1966; Oda and Kamiya, 1958), *Hanseniaspora valbyensis* (Braun and Snell, 1967) and *Torulopsis utilis* (Kulmacz and Schroepfer Jr., 1978) Phytosphingosine production has also been reported in the fungi *Aspergillus sydowi* and *Penicillium notatum* (Stodola and Wickerham, 1960).

Furthermore, in a study in which thirty species of yeast selected from the genera Saccharomyces, Kluyveromyces, Debaromyces, Pichia, Hansenula, Lipomyces, Sporobolomyces, Cryptococcus, Torulopsis, Candida, Trichosporon and Rhodotorula were examined, it was found that all contained at least a form of sphingolipids (ceramide monohexoside) and thus could potentially be employed for sphingolipid production (Kaneko et al., 1977). In an ethanolamine-producing mutant of *Saccharomyces cerevisiae*, phytosphingosine was shown to accumulate, thus providing this yeast with a source of ethanolamine (Ishida-Schick and Atkinson, 1983).

Sphingolipid production has also been demonstrated in strains of bacterial genera such as Sphingobacterium (Yano et al., 1983), Acetobacter, Bacteroides, Bdellovibrio, Xanthomonas and Flavobacterium (Tahara et al., 1986).

Stoffel et al. (1968) found that the yeast *Hansenula (Pichia) ciferrii* acetylates all of the long-chain bases which were used as precursors in the study. Sphingosine was converted into triacetylsphingosine and dihydrosphingosine into triacetyl-, diacetyl- and N-acetyl-dihydrosphingosine. Moreover, three acetyl derivatives of phytosphingosine have been isolated, namely tetraacetyl-, triacetyl- and N-acetyl-phytosphingosine. In addition to these acetyl derivatives, *Hansenula ciferrii* produced long chain ceramides in a medium containing long chain bases.

The biosynthetic pathway of tetraacetylphytosphingosine (TAPS) synthesis in *Pichia ciferrii* was described by Barenholz et al (1973). The biosynthetic pathway for sphingosine and dihydrosphingosine is proposed by Dimari et al. (1971).

Barenholz et al. (1971 & 1973) investigated the metabolic background of the production of TAPS and other sphingolipid bases in four strains of *Hansenula (Pichia) ciferrii*. In the later study, the profiles of four microsomal enzymes specific for the biosynthesis of acetylated sphingosine bases of a low (*Hansenula ciferrii* NRRL Y-1031, E-11, sex b, 8-20-57) and a high producer (*Hansenula ciferrii* NRRL Y-1031, F-60-10) were compared. It was found that the specific activity of 3-keto dihydrosphingosine synthetase and the long-chain base acetyl-CoA acetyltransferase were increased 5–10 fold and 30 fold respectively, as compared with the low producer, whereas the activities of palmityl thiokinase and 3-ketodihydrosphingosine reductase were similar. This indicates that in the low producer, the activity of the 3-ketodihydrosphingosine synthetase and the long-chain base acetyl-CoA acetyltransferase are the limiting steps in the synthesis of acetylated sphingosines. Under the defined growth conditions, *Hansenula ciferrii* NRRL Y-1031 F-60-10 was found to produce 300 $\mu$moles/l sphingosine (about 0.15 g/l) bases, of which, at least 250 $\mu$moles/l were extracellular. Even where culture conditions were optimized for TAPS production, only 0.485 g/l TAPS (0.024 g TAPS/g dry yeast) was obtained (Maister et al., 1962).

However, none of the yeast strains studied to date, even *Pichia ciferrii* NRRL Y-1031 F-60-10, produce sufficient amounts of sphingolipid bases such as sphingosine, phytosphingosine or derivatives thereof to be an efficient, economically attractive source of such compounds. For example, the availability of yeast strains capable of producing increased levels of TAPS would considerably improve the economic feasibility and attractiveness for the production of this important starting material which in turn may be converted into commercially valuable end-products such as ceramides, pseudoceramides and glycoceramides.

SUMMARY OF THE INVENTION

The present invention provides for the production of microbial strains capable of producing enhanced levels of sphingosine, dihydrosphingosine, phytosphingosine or derivatives thereof by means of mutagenesis and selection techniques. The thus-produced mutant strains produce enhanced levels of the desired products as compared to the production levels of their parent strains which are cultured under identical conditions. These increased production levels provide an economically attractive source of these compounds for use as such, or as starting materials for conversion into commercially valuable end-products.

DETAILED DESCRIPTION OF THE INVENTION

The present invention demonstrates that production of sphingosine, dihydrosphingosine, phytosphingosine and derivatives thereof can be increased by subsequent cycles of mutagenesis and selection of microbial strains which have been determined to produce such compounds. In this manner, biosynthetic bottlenecks can be removed step by step, resulting in the enhanced production of these products.

The present invention provides methods for the production of a microbial strain capable of producing enhanced levels of sphingosine, dihydrosphingosine, phytosphingosine and/or derivatives thereof as compared to its parent strain, wherein the parent strain is subjected to at least one mutagenesis treatment comprising treating said parent strain with a sufficient amount of a suitable mutagen to provide a mutant strain which is capable of producing enhanced levels of the desired product as compared to its parent strain when cultured under identical conditions; and subsequently selecting the mutant strain on the basis of enhanced production of the desired product.

In particular, mutant strains are produced which are capable of enhanced levels of sphingosine and/or keto, glycosylated or acetylated derivatives thereof including 3-ketosphingosine, triacetylsphingosine, diacetylsphingosine and N-acetylsphingosine; dihydrosphingosine and/or keto, glycosylated or acetylated derivatives thereof including 3-ketodihydrosphingosine, triacetyldihydrosphingosine, diacetyldihydrosphingosine and N-acetyldihydrosphingosine; and/or phytosphingosine and/or keto, glycosylated or acetylated derivatives thereof including tetraacetylphytosphingosine, triacetylphytosphingosine, diacetylphytosphingosine and N-acetylphytosphingosine. Preferred compounds are sphingosine, dihydrosphingosine, phytosphingosine and/or acetylated derivatives thereof. More preferred compounds are phytosphingosine and acetylated derivatives thereof. Most preferred is tetraacetylphytosphingosine (TAPS).

Preferably, the mutant strains produced by the methods of the present invention and cultured as described in the Examples (below) may produce an amount of 0.030 g TAPS/g yeast dry weight, preferably 0.050 g TAPS/g yeast dry weight, preferably 0.060 g TAPS/g yeast dry weight, preferably 0.075 g TAPS/g of yeast dry weight, preferably 0.10 g TAPS/g of yeast dry weight, preferably at least 0.15 g TAPS/g yeast dry weight, and most preferably at least 0.20 g TAPS/g yeast dry weight.

Strains (i.e. parent strains) which may be employed according to the present invention include yeast, bacterial and fungal strains capable of naturally producing sphingosine, dihydrosphingosine, phytosphingosine and/or derivatives thereof. Preferably, candidate (parent) strains for use in the process of the present invention are strains which demonstrate the highest inherent production levels of the desired products.

Yeast strains for use in the present invention may be selected from species of the genera Saccharomyces, Kluveromyces, Debaromyces, Pichia, Hansenula, Lipomyces, Sporobolomyces, Cryptococcus, Torulopsis, Endomycopsis, Candida, Trichosporon, Hanseniasprora and Rhodotorula. Preferred yeast strains belong to the genus Pichia, Hansenula, Endomycopsis, Candida, Saccharomyces and Hanseniaspora and particularly the species *Pichia ciferrii* (formerly indicated as *Hansenula ciferrii* and *Endomycopsis ciferrii*), *Candida utilis* and *Saccharomyces cerevisiae*. Most preferred are yeast strains which belong to the genus Pichia and most preferably to the species *Pichia ciferrii* (especially *Pichia ciferrii* NRRL Y-1031 F-60-10).

Preferred fungi are of the genera Aspergillus and Penicillium and are more preferably of the species *Aspergillus sydowi* and *Penicillium notatum*.

Preferred bacteria are of the genera Sphingobacterium (especially *S. versatilis, S. multivorum* and *S. mizutae*), Acetobacter (especially *A. xylinum*), Bacteroides (especially *B. melaninogenicus, B. fragilis, B. ruminicola* and *B. thetaiotaomicron*), Bdellovibrio (especially *Bdellovibrio bacteriovus*), Xanthomonas (especially *Xanthomonas campestris*) and Flavobacterium (especially *Flavobacterium devorans*).

According to the present invention, mutagenesis may be performed by using any suitable mutagen which leads to the enhanced production of sphingosine, dihydrosphingosine, phytosphingosine and/or derivatives thereof. Examples of preferred mutagens are UV irradiation, ethyl methane sulphonate and N-methyl-N'-nitro-N-nitrosoguanidine. (Stanbury, 1988; Shay, 1987; Masanari et al., 1985)

The mutagenesis may be carried out as a single mutagenesis, but it is found to be advantageous to perform the mutagenesis two or more times. The ability of strains to produce enhanced amounts of the desired products such as TAPS is elevated after each mutagenization step.

After the mutagenesis reaction(s) is completed, a resulting mutant can be selected which, when cultivated under conditions conducive to the production of the desired sphingosine, dihydrosphingosine, phytosphingosine and/or derivative thereof, demonstrates the highest production levels of the desired product. It is of general knowledge to the skilled person that the separation of desirable mutants from the very many inferior types is much easier for strains producing primary metabolites, e.g. amino acids, than for strains producing secondary metabolites (Stanbury, 1988).

Preselection of high-producing mutant cells is performed on agar plates by visual observation of the crystal zone of single colonies, followed by their isolation. Colonies showing the largest diameter of crystals relative to colony size are selected. Other preselection methods may also be employed, for example resistance to amino acid analogs or protein synthesis inhibitors.

Cells isolated in this manner may be cultured in shake flasks or tube cultures and appropriate mutants are selected by determining the production levels of the desired product via the analysis of suitable dilutions of the fermentation broth. The descriptions of the growth conditions, as detailed in the Examples, are provided as a reference for the determination of the production levels of the desired products by the strains of the present invention. However, other culture conditions, which are conducive to production of the desired products, as known to the skilled artisan, may also be used without departing from the spirit of the present invention.

Quantitative analysis may be performed by various methods, for example by means of the successive deacetylation of TAPS and related compounds via oxidation with periodate. Aldehydes, which are decomposition products of the oxidation of TAPS and related compounds, are formed in stoicheometric amounts.

Selection on the basis of TAPS production levels may additionally or alternatively be performed in shake flasks which are extracted with $CDCl_3$ and analyzed by NMR. TAPS is preferably used as a standard for NMR analysis.

Other desired products such as sphingosine, phytosphingosine and dihydrosphingosine; triacetyl, diacetyl and N-acetyl derivatives of sphingosine, phytosphingosine and dihydrosphingosine; glycosylated derivatives of sphingosine, phytosphingosine, and dihydrosphingosine; 3-keto dihydrosphingosine and/or 3-ketosphingosine may be quantitatively determined in the same manner and the TAPS standard used as the reference.

Once the desired product is obtained it may be used directly or may be further processed for eventual use. For example, acetylated derivatives of sphingosine, dihydrosphingosine and phytosphingosine may be deacetylated either enzymatically or chemically and subsequently used as starting materials in the synthesis of commercially valuable sphingolipid products such as ceramides, glycoceramides and pseudoceramides (Smeets and Weber, 1993).

In the following examples, efforts have been made to ensure accuracy with respect to numbers used (e.g., amounts, temperature, pH, etc.) but some experimental errors and deviation should be accounted for. Unless indicated otherwise, temperature is in degrees Celsius and pressure is at or near atmospheric.

PREPARATIVE EXAMPLE A

Preparation of a tetraacetylphytosphingosine Standard

A mixture of 1.0 g (2.8 mmol) phytosphingosine hydrochloride (Sigma), 2.7 ml (28 mmol) acetic acid anhydride, 2.1 ml (15 mmol) triethylamine and 10 ml pure chloroform is heated and stirred under a reflux during 8 hours. After cooling to room temperature, the mixture is washed with a saturated aqueous solution of sodium bicarbonate solution until a pH of 7 is obtained. The organic layer is subsequently dried on $MgSO_4$, filtrated and evaporated in vacuo at 50° C. The residue is purified by column chromatography using a Merck: Lobor Fertich Säule Groβe C (440-37) Lichroprep Si60 (40–60 μM) column. A mixture of dichloromethane and methanol (25:1) is used as eluent (pumping rate 10 ml/min.). The product obtained is a white solid and is formed in 80 percent yield and has a melting point in the range of 41–43° C. The purity of the thus-formed TAPS is determined in $CDCl_3$ by NMR techniques (proton NMR, 360 MHz) (p-nitrotoluene was used as the internal standard) and is estimated to be 96%.

A concentration of 15 mg TAPS/ml $CDCl_3$ derived as indicated above is used as a standard in all the examples as described in the present invention.

PREPARATIVE EXAMPLE B

TAPS Agar Medium Slants 122 g Nemoutex (Diastatische Produkten B. V.; Leiden, The Netherlands) is dissolved in 1 l water and sterilized for 60 minutes at 110° C. The suspension is incubated at room temperature overnight and filtered to remove the solid particles. The pH is poised at 6.4. 10 g/l agar (Bacto) is added and the solution is sterilized at 120° C. for 30 min.

PRAPARATIVE EXAMPLE C

| TAPS medium (for tube cultures and shake flasks) | |
|---|---|
| Compound | amount (g/l) |
| KH-phtalate | 20 |
| NaCl | 0.06 |
| $MgSO_4.7H_2O$ | 9.88 |
| $CaCl_2.2H_2O$ | 20 |
| $NH_4Cl$ | 4.83 |
| $KH_2PO_4$ | 1.0 |
| $(NH_4)_2Fe(SO_4)_2$ | 0.027 |
| $ZnSO_4$ | 0.005 |
| $CuSO_4$ | 0.0075 |
| $MnSO_4$ | 0.0006 |
| $H_3BO_3$ | 0.0006 |
| Na-molybdate | 0.0006 |
| KI | 0.00015 |
| Myo-inositol | 0.059 |
| nicotinic acid | 0.003 |
| Ca-D-Panthotenate | 0.003 |
| vitamine $B_1$ | 0.003 |
| P-aminobenzoate | 0.002 |
| vitamine $B_6$ | 0.0003 |
| biotine | 0.00001 |
| yeast extract (Difco) | 1.0 |

In shake flasks and culture tubes, glucose is added to final concentrations of 33 and 7 g/l, respectively. After the components are dissolved, the pH is adjusted to 5.4.

100 ml conical flasks (without baffle) are filled with 30 ml of medium and sterilized at 110° C. for 30 minutes. For agar plates, 20 g agar (Bacto) is added to the medium and the same sterilization procedure is used.

PREPARATIVE EXAMPLE D

| YEP-D medium | |
|---|---|
| Bactopeptone | 20 g |
| Yeast extract | 10 g |
| glucose | 20 g |
| bacto-agar | 20 g |

A volume of 1000 ml demineralized water is added and the pH is poised at 7.0. The medium is sterilized for 30 minutes at 110° C.

PREPARATIVE EXAMPLE E

Physiological Salts Medium

In 1 liter demineralized water, 8.5 g NaCl is dissolved and sterilized for 20 minutes at 120° C.

PREPARATIVE EXAMPLE F

Growth Conditions for Cell Culture

*Pichia ciferrii* NRRL Y-1031 F-60-10 and mutants thereof are grown on slants or agar plates at 24° C. in an incubator.

Growth in tubes is performed in 40 ml glass tubes (diameter 2.5 cm) containing 3.0 ml TAPS medium. The tubes are incubated vertically in a rack in a Gallenkamp orbital incubator (300 rpm, 24° C.) for a period of 3 days. After the fermentation is completed, the concentration of the thus-formed TAPS is corrected for evaporation during the incubation. The mutants are tested in four-fold.

Growth in shake flasks (without a baffle) is performed in 30 ml TAPS medium (see above) in 100 ml conical flasks or in 100 ml medium in 500 ml conical flasks. Incubation occurs in a Gallenkamp orbital incubator (250 rpm, 24° C.) for a period of 3 days. After the fermentation is completed, the concentration of the thus-formed TAPS is corrected for evaporation during the incubation. The mutants are tested in four-fold.

EXAMPLE 1

Mutagenesis with Ultra-Violet Irradiation (UV)

A semi-logarithmic culture (100 ml) of *Pichia ciferrii* NRRL Y-1031 F-60-10 or a mutant derived thereof is grown on YEP-D or TAPS medium (24 hours, 24° C., 250 rpm). The culture is centrifuged (Heraeus sepatech minifuge RF centrifuge, 5,000×g, 5 minutes) and the pellet washed twice with 25 ml physiological salt medium. The cell suspension is diluted to a final concentration of $10^8$ cells/ml and 10 ml of the suspension is pipetted into sterile petri disks (diameter 9 cm). The plates are then subjected to UV radiation at a distance of 23 cm from the irradiation source (Osram lamp HQV, 125 watt) and respectively irradiated for 0, 15, 30, 60 and 90 seconds. The irradiated cells are then placed in the dark (30 minutes, 20° C.). To determine the survival rate, dilutions of the mutated cell suspensions are plated out on YEP-D agar medium. The remaining cell suspensions are grown on TAPS medium overnight. If desired, glycerol may be added to an final concentration of 10% and the suspensions stored at −20° C. After 3 days of incubation at 24° C., the colonies are counted and the survival percentage is calculated. The cell suspension wherein the irradiation treatment results in a survival percentage of about 10% is used for selection of high TAPS-producing mutants.

EXAMPLE 2

Mutagenesis with Ethyl-Methane-Sulphonate (EMS)

A semi-logarithmic culture (100 ml) of *Pichia ciferrii* NRRL Y-1031 F-60-10 or a mutant derived thereof is grown and washed as described in Example 1, with the modification that the pellet is washed with 50 ml 1M Tris-HCl pH 7.5 instead of physiological salt medium. Afterwards, the cells are diluted in 25 ml of 1.0M Tris-HCL buffer pH 7.5 to a final concentration of $10^8$ cells/ml.

To a 6 ml cell suspension, 300 μl EMS is added and incubated at room temperature. At time intervals of 0, 1, 3, 6 and 12 minutes, 1 ml samples are drawn. The cells are subsequently washed twice with 9 ml physiological salts medium and appropriate dilutions are plated out on YEP-D agar medium. Overnight growth of the remaining mutated cells and the estimation of the survival percentage are performed as described in Example 1. The sample showing 10 percent survival is selected to isolate high TAPS producing mutants.

EXAMPLE 3

Mutagenesis with N-methyl-N'-nitro-N-nitrosoguanidine (NTG)

A semi-logarithmic culture (100 ml) of *Pichia ciferrii* NRRL Y-1031 F-60–10 or a mutant derived thereof is grown and washed as described in Example 1, with the modification that the pellet is washed with 50 ml 1M Tris-HCl pH 7.5 instead of physiological salt medium. Afterwards, the cells are diluted in 25 ml of 1.0M Tris-HCL buffer pH 7.5 to a final concentration of $10^8$ cells/ml.

To 6 ml cell suspension, 600 μl of a freshly prepared stock solution of NTG is added and incubated at room temp. At time intervals of 0, 1, 3, 6 and 12 minutes, 1 ml samples are drawn. The cells are subsequently washed twice with 9 ml physiological salt medium and appropriate dilutions are plated out on YEP-D agar medium. Overnight growth of the mutated cells and the estimation of the survival percentage are performed as in Example 1. The sample showing 10 percent survival is selected to isolate high TAPS producing mutants.

EXAMPLE 4

Preselection of Mutants

Preselection is performed on TAPS-agar medium. Appropriate dilutions of cells (25–50 colonies/plate) are obtained as described in Examples 1, 2, or 3, above, and are incubated 4–7 days at 24° C. in an incubator. To stimulate crystallization, the plates are incubated at 4° C. overnight. Afterwards, colonies having the highest crystallization ratio are selected (Crystallization ratio=diameter crystallization zone surrounding the colony (mm)/diameter colony (mm)).

These colonies are isolated and transferred to agar plates containing TAPS-agar medium. These plates are referred to as "master plates" and the colonies are indicated as "original colonies". The cell-material on these master plates is used for selection of the highest TAPS producers in tubes, shake flasks and storage purposes.

EXAMPLE 5

TAPS Analysis on Tube-Grown Cultures (Method 1)

Further selection of cells obtained in Example 4 is subsequently carried out in tubes and shake flasks as is described under Preparative Example F and the analysis is performed as indicated below. The procedure of TAPS determination is divided in three parts (sections 5a–c).

5a Deacetylation of Tetraacetylphytosphingosine

Stock solutions of 0.05–0.3 g/l TAPS are used as references. To 1 ml of the samples, sodium hydroxide is added to an eight-fold excess with regard to the expected amount of TAPS and the solution is incubated at 50° C. during two hours.

5b Oxidation of Phytosphingosine

Oxidation of phytosphingosine is performed by the addition of sodium periodate.

$$CH_3-(CH_2)_{13}-CHOH-CHOH-CHNH_2-CH_2-OH \rightarrow CH_3-(CH_2)_{13}-CHO+2\ HCOOH+NH_3+HCHO$$

A sample of the deacetylated reaction mixture obtained in step a, above is added to 1 ml of a 30 mM potassium periodate in 0.1M acetic acid buffer pH 5.4. Subsequently, the oxidation is carried out at room temperature in the dark overnight during which the reaction mixture is shaken gently on an IKA Vibrax VXR electronic shaker (125 rpm). The reaction tubes are carefully closed to prevent evaporation of the aldehyde generated in the reaction.

5c Determination of Aldehyde

The amount of aldehyde generated in step b, above may be determined by a calorimetric method as described by Avigad (1983).

Following the oxidation procedure of step b, 0.3 ml 1% (w/v) Purpald (Aldrich) in 1N NaOH is added to 0.2 ml sample. The Purpald reagent should be freshly prepared (not older than 2 hours). This mixture is incubated for 30 minutes on an IKA Vibrax VXR electronic shaker (180–200 rpm). The reaction is subsequently terminated by the addition of 0.5 ml 0.2% $NaBH_4$ in 1N NaOH (w/v). The absorption of the sample is measured at a wavelength of 548 nm.

EXAMPLE 6

TAPS Analysis by NMR (Method 2)

Further selection of cells obtained in Example 4 is subsequently carried out in tubes and shake flasks as is described under Preparative Example F and the analysis is performed as indicated below.

6a Extraction

Extraction of TAPS from the shake flask growth medium may be performed with various hydrophobic organic compounds. The organic extraction compound applied in the present example is deuterated chloroform ($CDCl_3$). Culture medium (25 ml) is extracted with 2 ml $CDCl_3$ and mixed horizontally in a vigorous manner at room temperature on an IKA Vibrax VXR electronic shaker (full speed)) for 5 minutes. The mixture is then centrifuged (Heraeus sepatech minifuge RF centrifuge, 10,000×g, 5 minutes) and the $CDCl_3$ removed and analyzed by NMR.

6b Nuclear Magnetic Resonance (NMR) Analysis

The TAPS content of the $CDCl_3$-layer is measured in the same series as the TAPS standard and for this purpose an AMR360 NMR-apparatus (Bruker-Carlsruhe Germany) is used. The following adjustments of the NMR apparatus are used:

Receiver gain value: fixed
Relaxation time: 5 seconds
Number of scans: fixed
Pulse: 45°

The Fourier transformation of the obtained FID's (Free Induction Decay) are performed with an absolute intensity. The quantity of TAPS (expressed in mg per gram culture) is calculated with the following formula:

$$\frac{\text{Integral (sample)}}{\text{Integral (standard)}} \times \text{weight standard} \times \text{purity standard} \times 2/25$$

The weight and the purity of the standard is expressed in grams and percent, respectively. The standard contains 15 mg TAPS/ml $CDCl_3$.

EXAMPLE 7

Dry Weight Measurement

Dried centrifuge tubes with known weights (A) are filled with about 10 ml cell suspension and the weight is measured once more (B) and centrifuged. The pellets are subsequently dried in an incubator (24 hours, 105° C.) and the weight measured again (C). The dry weight is calculated as follows (A, B, C. are expressed in grams):

dry weight (g/kg)={(C−A)/(B−A)}×1000 g dry matter/kg cell suspension.

For shake flasks, the TAPS content (in gram TAPS/gram dry weight) is calculated as follows:

$$TAPS \text{ content} = \frac{\text{Quantity } TAPS \text{ (g } TAPS/\text{kg culture)}}{\text{Yeast dry weight (g/kg culture)}}$$

Accordingly, the production levels of TAPS are expressed as g TAPS/g yeast dry weight.

EXAMPLE 8

Quantitative Determination of TAPS Formed by the Cultures of *Pichia ciferrii* NRRL Y-1031 F-6010 and obtained mutants on TAPS medium

*Pichia ciferrii* NRRL Y-1031 F-60-10 is grown in forty-fold, CBS 111, CBS 1710 and CBS 1910 are grown in ten-fold and mutant strains are grown in five-fold in shake flasks on TAPS medium and cultured under conditions as described under Preparative Example F. TAPS extraction and NMR-analysis are performed as described in Example 6. Dry weight measurement, is performed as described in Example 7.

The resonance peaks of the NMR spectra of the $CDCl_3$-layer which are obtained by extraction of a culture of a TAPS-producing yeast strain are located identically to those which are obtained from analysis of the TAPS-standard which is prepared as described in Preparative Example A.

The average productivity of the forty shake flask cultures of F-60-10 is 0.025 g TAPS/g yeast dry weight. The productivity of CBS 111, CBS 1710 and CBS 1910 is the average of 10 independent measurements and the productivities of mutant strains are the averages of 5 independent measurements. The productivities of five mutant strains (designated as 5F11, 14D11, 15G8, 20A11 and 27D10) are depicted in the table below. As is shown, the mutant strains have a considerable higher production level, about 40–60% higher, than the productivity of the parent strain.

The five mutant strains, and also the parent strain *Pichia ciferri* NRRL-Y1031 F-60-10, are deposited at the "Centraal Bureau voor Schimmelcultures" (CBS), Baarn, the Netherlands, at Jul. 6, 1994, under the following deposition numbers (see also table above): CBS 403.94, CBS 404.94, CBS 405.94, CBS 406.94, CBS 407.94 (mutant strains) and CBS 408.94 (parent strain).

Pursuant to the applicable requirements of U.S. patent law, as of the issue date of the present patent, all restrictions imposed on the availability to the public of these deposited materials will be irrevocably removed. TAPS-productivity in shake flasks of *Pichia ciferrii* strains CBS 111, CBS 1710 and CBS 1910, and of NRRL-Y1031 F-60-10 and mutants obtained from the latter strain:

|  | Strain | Productivity (g TAPS/g dry weight) |
|---|---|---|
|  | CBS 111 | 0.0072 |
|  | CBS 1710 | 0.0046 |
|  | CBS 1910 | ND* |
| F-60-10 | CBS 408.94 | 0.023 |
| 5F11 | CBS 405.94 | 0.033 |
| 14D11 | CBS 403.94 | 0.037 |
| 15G8 | CBS 404.94 | 0.034 |
| 20A11 | CBS 406.94 | 0.036 |
| 27D10 | CBS 407.94 | 0.032 |

*ND = not detectable

LITERATURE

Avigad G (1983) Anal. Biochem. 134: 499–504.
Barnett J A, Payne R W and Yarrow D (1990) in *Yeasts: characteristics and identification* 2nd edition (Cambridge University Press; Cambridge) pp. 66, 67 and 474.
Barenholz Y, Edelman I and Gatt S (1971) Biochim. Biophys. Acta 248: 458–465.
Barenholz Y, Gadot, N, Valk E and Gatt S (1973) Biochim. Biophys. Acta 306 (2): 341–345.
Braun P E and Snell E (1968) J. Biol. Chem. 243: 3775–3783.
Curatolo W (1987) Pharm. Res. 4: 271–277.
Dimari S J, Brady R N and Snell E E (1971) Arch. Biochem. Biophys. 143: 553–565.
Kaneko H, Hosohara, M, Tanaka M and Itoh T (1977) Lipids 11: 837–844.
Kerscher M, Korting H C., Schäfer-Korting M (1991) Eur. J. Dermatol. 1: 39–43.
Kulmacz R J and Schroepfer, Jr. G J (1978) Biochem. Biophys. Res. Commun. 82: 371–377.
Maister H G, Rogovin S P, Stodola F H and Wickerham L J (1962) Appl. Microbiol. 10: 401–406.
Oda T and Kamiya H (1958) Chem. Pharm. Bull. 6: 682.
Smeets J W H and Weber P G (1993) WO 93/20038.
Stodola F H and Wickerham L J (1960) J. Biol. Chem. 235: 2584–2585.
Stoffel W, Sticht G and Lekim D (1968) Hoppe-Seyler's Z. Physiol. Chem. 349: 1149–1156.
Tahara Y, Nakagawa A and Yamada Y (1986) Agric. Biol. Chem. 50: 2949–2950.
Wagner H and Zofcsic W (1966) Biochemische Zeitschrift 344: 314–316.
Wickerham L J (1951) Tech. Bull. 1029, 56.
Wickerham L J and Burton K A (1954) J. Bacteriol. 67: 303–308.
Wickerham L J and Stodola F H (1960) J. Bacteriol. 80: 484–491.
Yano I, Imaizumi S, Tomiyasu I and Yabuuchi E (1983) FEMS Microbiol. Lett. 20: 449–453.

We claim:

1. A method for producing a mutant strain of Pichia that is capable of producing at least 0.030 g tetraacetyl-phytosphingosine (TAPS)/g Pichia dry weight comprising the steps of:
   a) obtaining a parent strain of Pichia that is capable of naturally producing TAPS;
   b) treating said parent Pichia strain with a mutagen;
   c) selecting a mutant strain of Pichia, wherein said mutant strain is capable of producing at least 0.030 g TAPS/g Pichia dry weight when cultured in liquid TAPS medium for a period of 3 days at 24° C. in a conical flask placed on an orbital incubator at 250 rpm.

2. The method of claim 1, wherein said parent Pichia strain is of the species *Pichia ciferri*.

3. The method of claim 1, wherein said mutagen is selected from the group consisting of UV radiation, ethyl methane sulfonate or N-methyl-N'-nitro-N-nitrosoguanidine.

4. An isolated Pichia strain capable of producing at least 0.030 g TAPS/g Pichia dry weight when cultured in liquid TAPS medium for a period of 3 days at 24° C. in a conical flask placed on an orbital incubator at 250 rpm.

5. The isolated Pichia strain of claim 4, wherein said Pichia strain is of the species *Pichia ciferri*.

6. An isolated mutant Pichia strain capable of producing at least 0.030 g TAPS/g Pichia dry weight when cultured in liquid TAPS medium for a period of 3 days at 24° C. in a conical flask placed on an orbital incubator at 250 rpm, wherein said strain is produced by the steps of:
   a) obtaining a parent strain of Pichia that is capable of naturally producing TAPS;
   b) treating said parent Pichia strain with a mutagen;
   c) selecting an mutant strain of Pichia, wherein said mutant strain is capable of producing at least 0.030 g TAPS/g Pichia dry weight under said conditions.

7. The isolated Pichia strain of claim 6, wherein said strain is selected from the group consisting of CBS 403.94, CBS 404.94, CBS 405.94, CBS 406.94 and CBS 407.94, deposited at the Centraal Bureau voor Schimmelcultures, Baarn, the Netherlands.

8. A method for producing a compound selected from the group consisting of sphingosine, dihydrosphingosine, and phytosphingosine, or a derivative of any thereof, comprising the step of culturing a Pichia strain of claim 4 under conditions in which said compound is produced.

9. A method for producing a compound selected from the group consisting of sphingosine, dihydrosphingosine, and phytosphingosine, or a derivative of any thereof, comprising the step of culturing a Pichia strain of claim 6 under conditions in which said compound is produced.

10. An isolated Pichia strain selected from the group consisting of CBS 403.94, CBS 404.94, CBS 405.94, CBS 406.94 and CBS 407.94, deposited at the Centraal Bureau voor Schimmelcultures, Baam, the Netherlands.

11. A method for producing a compound selected from the group consisting of sphingosine, dihydrosphingosine, and phytosphingosine, or a derivative of any thereof, comprising the step of culturing a Pichia strain of claim 10 under conditions in which said compound is produced.

12. The isolated Pichia strain of claim 6, wherein said Pichia strain is of the species *Pichia ciferri*.

13. An isolated mutant Pichia strain wherein said strain is produced by the steps of:
   a) obtaining a parent strain of Pichia that is capable of naturally producing TAPS;
   b) treating said parent Pichia strain with a mutagen; and
   c) selecting a mutant strain of Pichia that is capable of producing an amount of TAPS that is at least about 50% greater/g Pichia dry weight than may be produced from said parent strain when compared under identical conditions, and wherein
   said mutant strain is also capable of producing at least 0.030 g TAPS/g Pichia dry weight when cultured in liquid TAPS medium for a period of 3 days at 24° C. in a conical flask placed on an orbital incubator at 250 rpm.

14. A method for producing a mutant strain of Pichia comprising the steps of:
   a) obtaining a parent strain of Pichia that is capable of naturally producing TAPS;
   b) treating said parent Pichia strain with a mutagen; and
   c) selecting a mutant strain of Pichia that is capable of producing an amount of TAPS that is at least about 50% greater/g Pichia dry weight than may be produced from said parent strain when compared under identical conditions, and wherein
   said mutant strain is also capable of producing at least 0.030 g TAPS/g Pichia dry weight when cultured in liquid TAPS medium for a period of 3 days at 24° C. in a conical flask placed on an orbital incubator at 250 rpm.

15. An isolated Pichia strain capable of producing at least 0.10 g TAPS/g Pichia dry weight when cultured in liquid TAPS medium for a period of 3 days at 24° C. in a conical flask placed on an orbital incubator at 250 rpm.

16. An isolated Pichia strain capable of producing at least 0.20 g TAPS/g Pichia dry weight when cultured in liquid TAPS medium for a period of 3 days at 24° C. in a conical flask placed on an orbital incubator at 250 rpm.

17. A method for producing a compound selected from the group consisting of sphingosine, dihydrosphingosine, and phytosphingosine, or a derivative of any thereof, comprising the step of culturing in a liquid medium a composition, which composition includes a Pichia strain capable of producing at least 0.030 g TAPS/g Pichia dry weight when cultured in liquid TAPS medium for a period of 3 days at 24° C. in a conical flask placed on an orbital incubator at 250 rpm, under conditions in which said compound is produced.

* * * * *